US011045262B2

(12) United States Patent
Mitra et al.

(10) Patent No.: US 11,045,262 B2
(45) Date of Patent: Jun. 29, 2021

(54) FIXATION-FREE ROBOTIC SURGERY

(71) Applicant: Smith & Nephew, Inc., Memphis, TN (US)

(72) Inventors: Riddhit Mitra, Pittsburgh, PA (US); Branislav Jaramaz, Pittsburgh, PA (US); Samuel Dumpe, Pittsburgh, PA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/615,023

(22) PCT Filed: May 21, 2018

(86) PCT No.: PCT/US2018/033709
§ 371 (c)(1),
(2) Date: Nov. 19, 2019

(87) PCT Pub. No.: WO2018/213835
PCT Pub. Date: Nov. 22, 2018

(65) Prior Publication Data
US 2020/0078098 A1 Mar. 12, 2020

Related U.S. Application Data

(60) Provisional application No. 62/508,825, filed on May 19, 2017.

(51) Int. Cl.
*A61B 34/20* (2016.01)
*A61B 34/30* (2016.01)
(Continued)

(52) U.S. Cl.
CPC ............ *A61B 34/20* (2016.02); *A61B 17/157* (2013.01); *A61B 34/30* (2016.02); *A61B 17/1764* (2013.01);
(Continued)

(58) Field of Classification Search
CPC ...... A61B 17/157; A61B 17/154; A61B 34/20
See application file for complete search history.

(56) References Cited

U.S. PATENT DOCUMENTS 6,090,114 A * 7/2000 Matsuno ............... A61B 17/157
606/86 R
7,377,924 B2 * 5/2008 Raistrick ............... A61B 17/154
606/87
(Continued)

FOREIGN PATENT DOCUMENTS

EP 1634536 A2 3/2006
WO 2016173626 A1 11/2016

OTHER PUBLICATIONS

International Search Report and Written Opinion for PCT/US2018/033709 dated Aug. 29, 2018.

*Primary Examiner* — Andrew Yang
(74) *Attorney, Agent, or Firm* — Troutman Pepper Hamilton Sanders LLP

(57) ABSTRACT

A cut guide assembly (600) and a system for mounting assembly on a patient are described. The system includes an ankle clamp (525), an alignment guide (530) configured to be removably attached to the ankle clamp, and the cut guide assembly. The cut guide assembly includes a cut guide (535) and a position tracker (200). The cut guide includes a receiving feature (605) configured to removably attach to at least a portion of the alignment guide, a locking mechanism (610) configured to lock the receiving feature to the at least a portion of the alignment guide, and a plurality of pin receptacles (620), each of the plurality of pin receptacles configured to receive a bone pin (540) configured to affix the cut guide to a patient's bone. The position tracker configured to be affixed to the cut guide when the cut guide is affixed to the patient's bone.

19 Claims, 5 Drawing Sheets

(51) Int. Cl.
*A61B 17/15* (2006.01)
*A61B 90/00* (2016.01)
*A61B 17/17* (2006.01)
*A61B 17/84* (2006.01)

(52) U.S. Cl.
CPC ..... *A61B 17/846* (2013.01); *A61B 2034/2072* (2016.02); *A61B 2090/3983* (2016.02)

(56) References Cited

U.S. PATENT DOCUMENTS

| | | | |
|---|---|---|---|
| 7,670,345 B2 * | 3/2010 | Plassky | A61B 17/157 606/88 |
| 2008/0183176 A1 | 7/2008 | Canonaco et al. | |
| 2017/0071677 A1 | 3/2017 | Utz et al. | |

* cited by examiner

FIXATION-FREE ROBOTIC SURGERY

CROSS-REFERENCE TO RELATED APPLICATION

This application is a U.S. national stage filing under 35 U.S.C. § 371 of International PCT Application No. PCT/US2018/033709, filed May 21, 2018, which claims the benefit of priority to U.S. Provisional Application No. 62/508,825 titled "Fixation-Free Robotic Surgery," filed May 19, 2017, each of which is incorporated herein by reference in its entirety.

TECHNICAL FIELD

The present disclosure is generally related to apparatuses, systems and methods for computer-aided orthopedic surgery. More specifically, the present disclosure is related to automatically determining the position and orientation of an implant for a patient in advance of joint replacement surgery.

BACKGROUND

The use of computers, robotics, and imaging to aid orthopedic surgery is known in the art. There has been a great deal of study and development of computer-aided navigation and robotic systems used to guide surgical procedures. For example a robotic surgery system can assist the surgeon in accurately cutting a bone into a desired shape. In procedures such as total hip replacement (THR), computer-aided surgery techniques have been used to improve the accuracy and reliability of the surgery. Orthopedic surgery guided by images has also been found useful in preplanning and guiding the correct anatomical position of displaced bone fragments in fractures, along a good fixation by osteosynthesis.

Cut guides or cutting blocks can be used in an orthopedic surgical procedure to assist a surgeon in cutting or modifying some portions of a target bone. For example, in joint replacement surgeries, such as THR or total knee replacement (TKR), the preparation of the bones can involve temporarily affixing saw guide cutting blocks to the bones so that a reciprocating saw blade can be held steady along its intended path. Placement of these blocks can be guided by manual instrumentation or through the use of jigs.

The positioning of cutting blocks can be a time consuming and complicated process, which is critical to positive outcomes for the patient. Mechanisms that allow the cutting blocks to be adjusted within the required workspace are complex, and require high machining tolerances, adding to the costs and complexity of these instrument systems. Such instruments are also expensive to create and manage, and result in significant operational costs to maintain and clean. These costs increase the burden of managing cutting blocks. Mechanical referencing instruments can also add to the burden of managing cut guides or cutting blocks.

Manual alignment of these blocks can be cumbersome and is limited to information obtainable through mechanical and visual referencing means. The instruments used to manually align cutting blocks cannot fully capture the 3D shape of the bones, nor can they adequately capture information about kinematics of the joint or soft tissue tension or laxity.

Some surgery tracking systems and robotic-assisted surgery techniques include tracking rigid bodies with fixation pins for attachment and tracking of the femur and tibia bones in orthopaedics. Typically, 3-5 mm bi-cortical bone screws or smaller uni-cortical screws are inserted into the patient's bone(s) for tracker attachment. The tracker can then be registered and, by measuring movement of the tracker in space, the surgery tracking system can accurately measure the location of the patient during a procedure. However, the attachment of the tracker can be an added burden during the surgical procedure. Use of these screws can also be considered an undesirable addition to the invasiveness of the surgery.

SUMMARY

There is provided a system for mounting a cut guide on a patient during a surgical procedure. The system includes an ankle clamp configured to clamp to a patient's ankle, an alignment guide configured to be removably attached to the ankle clamp, a cut guide, and a position tracker. The cut guide includes a receiving feature configured to removably attach to at least a portion of the alignment guide, a locking mechanism configured to lock the receiving feature to the at least a portion of the alignment guide, and a plurality of pin receptacles, each of the plurality of pin receptacles configured to receive a bone pin configured to affix the cut guide to a patient's bone. The position tracker configured to be affixed to the cut guide when the cut guide is affixed to the patient's bone.

In some embodiments, the ankle clamp is configured to adjustably rotate about the patient's ankle to adjust an angle of the alignment guide.

In some embodiments, the alignment guide includes an extramedullary alignment guide configured to be positioned adjacent to a patient's tibia.

In some embodiments, the position tracker includes a mounting feature configured to be inserted into the receiving feature of the cut guide upon removal of the at least a portion of the alignment guide. In some additional embodiments, the locking mechanism is further configured to lock the receiving feature to the mounting feature of the position tracker.

In some embodiments, the position tracker includes a plurality of position markers. In some additional embodiments, the plurality of position markers include reflective markers. In some additional embodiments, the position tracker includes a frame, and wherein the plurality of position markers is mounted on the frame. In some additional embodiments, the plurality of position markers are mounted in a known pattern for tracking by a surgical navigation system.

In some embodiments, the cut guide includes a tibia cut guide. In some additional embodiments, the tibia cut guide includes a guide slot configured to guide a cutting too to resect a patient's tibia.

There is also provided a cut guide assembly. The assembly includes a position tracker including a mounting feature and a cut guide. The cut guide includes a receiving feature configured to receive at least a portion of the mounting feature, a locking mechanism configured to lock the receiving feature to the at least a portion of the mounting feature, and a plurality of pin receptacles, each of the plurality of pin receptacles configured to receive a bone pin configured to affix the cut guide to a patient's bone.

In some embodiments, the position tracker includes a plurality of position markers. In some additional embodiments, the plurality of position markers include reflective markers. In some additional embodiments, the position tracker includes a frame, and wherein the plurality of position markers is mounted on the frame. In some additional embodiments, the plurality of position markers are mounted in a known pattern for tracking by a surgical navigation system.

In some embodiments, the cut guide includes a tibia cut guide. In some additional embodiments, the tibia cut guide includes a guide slot configured to guide a cutting too to resect a patient's tibia.

The example embodiments as described above can provide various advantages over prior techniques. For example, the techniques as taught herein can reduce the time required for mounting a tibia cut guide for a knee replacement surgery. The techniques also provide for reducing the number of cortical pins used during a knee replacement surgery.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
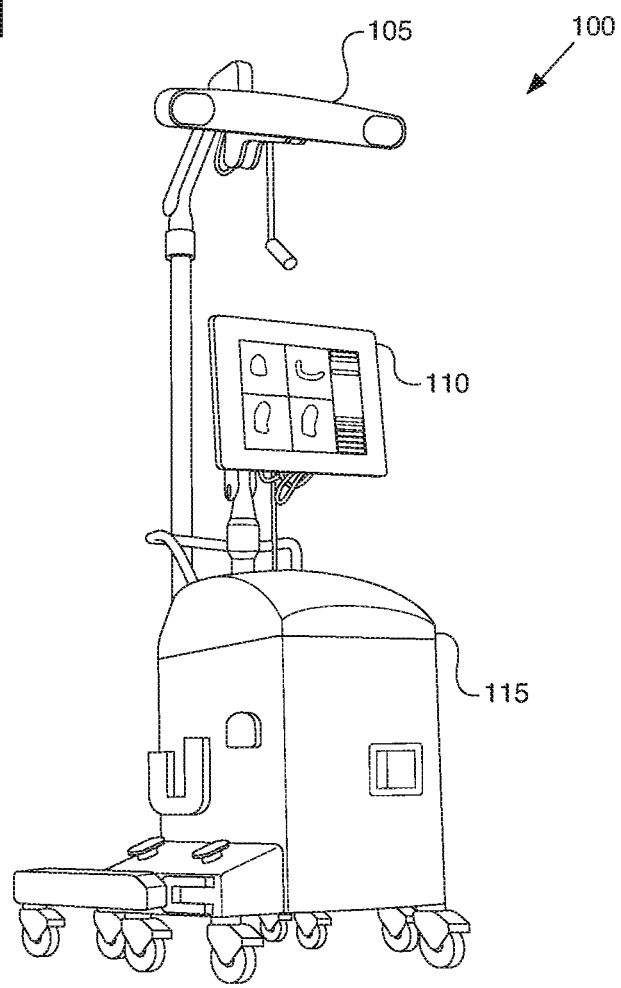
FIG. 1 depicts an illustrative navigation system in accordance with certain embodiments.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Total knee replacement surgery requires several precise cuts to be made in the femur and tibia in order for the chosen implant to fit correctly and to restore the geometry and kinematics of a natural healthy knee. To perform these steps, in both conventional (manual method) and Computer Aided Surgery (CAS) total knee replacement, a series of guide blocks are used that provide a drill or cutting guide to assist the surgeon to perform the steps required to prepare the femur and tibia for receiving the implant.

The conventional manual instrumented method used to prepare the femur for a knee replacement implant, outlined below as an example, generally includes fastening a distal cutting guide block on the femur, generally located by an intramedullary pin (IM rod) or screw inserted into the distal end of the femur and locating the distal guide block in the desired position, such position providing the correct implant varus-valgus and transverse rotational angle about the IM rod and the proper amount of distal resection; aligning a distal cutting guide, whether being integral with the guide block or a separate element configured to fasten thereto, in a predetermined location relative to the distal guide block reference position and inserting locating pins through the distal cutting guide and into the femoral condyles to fasten the cutting guide in place on the anterior surface; making the distal cut to resect the predetermined amount of bone from the distal end of the condyles; positioning a second femoral implant sizing guide (the femoral sizer) freely on the newly cut distal surface of the femur and ensuring that the anticipated resection level for the anterior cut, the anterior-posterior adjustment (referencing off either the existing posterior condyle or the anterior femur) for correct implant sizing, and that the rotational alignment and medial-lateral position of the positioning block are all correct before fixing the 4-in-1 cutting guide block in place with pins, drilling the implant peg holes; and performing the anterior and posterior cuts, and subsequently making the anterior-posterior chamfer and notch cuts. Note that adjusting rotation of the implant in the sagittal plane is generally not possible with the IM rod based instruments typically in use today. Thus, a femoral implant's position in knee extension is normally set in a fixed relationship to the IM rod axis.

The steps required to prepare the tibia are less involved. Generally, they include: aligning a guide rail relative to the mechanical axis of the tibia; obtaining proper rotational (varus-valgus) alignment of the guide block and fastening the guide block in place to the anterior surface of the proximal end of the tibia; further adjusting the vertical and angular position of the tibial guide block to ensure that the desired posterior slope and level of tibial resection are provided; inserting location pins using the guide block to fix its position on the tibia; removing the guide block and replacing it with a tibial resection cutting guide that is retained in place with the location pins; and resecting the chosen amount of tibial bone. Note that the final position of the tibial plate implant is not determined by this step, only the planar surface on which it will rest. Anterior-posterior (AP), medial-lateral (ML), and rotational positioning of the tibial plate implant are subsequently determined by the surgeon's judgment as to its best fitting location on the resected tibia after the femoral implant has been located and fixed to the resected femur.

The above described surgical procedure remains generally similar whether traditional or computer assisted surgery is being performed. A CAS system can employ passive or active trackable elements affixed to surgical tools and patient bone references to permit the determination of position and orientation of these tools and bones in three-dimensional space. In certain types of CAS, preoperatively taken images or computer generated models created from preoperative patient scans can be used to provide accurate patient specific anatomical information. The images or models can be used to register or calibrate the real-time position of the same patient's anatomical elements. This can permit subsequent tracking of the patient's anatomical elements and display of these anatomical elements relative to the surgical tools used during the surgery.

As noted above, when mounting tracking attachments for computer aided surgery, the position trackers are typically pinned directly to the bone. Thus, for a knee replacement surgery, a femur tracking attachment is pinned to the patient's femur, and a tibia tracking attachment is pinned to the patient's tibia. The attachment of the pins for the tracking attachments not only add to the setup time for the procedure, but also increase the risk of infection and fracture. Fracture risk becomes an increasingly likely outcome when dealing with a smaller bone such as the tibia.

The present disclosure is directed to techniques for mounting a tracker or tracking attachment directly to a previously mounted cut guide during a joint replacement procedure. For example, in a total knee replacement, the tibia tracker can be directly mounted to a previously mounted tibia cut guide, thereby eliminating a need to pin the tibia tracker to the patient's tibia itself. As described in greater detail below, standard ankle clamps and extramedullary alignment guides can be used to position the tibia cut guide according to standard mounting procedures. Once the tibia cut guide is attached, the tibia tracker can be attached directly to the tibia cut guide and used to provide anatomic and soft tissue data to the navigation or robotic-assisted surgical system, such as the navigation system described below in the description of FIG. 1.

FIG. 1 depicts an illustrative navigation system in accordance with certain embodiments. As shown in FIG. 1, the navigation system 100 can include a tracking device 105. In some embodiments, the navigation system 100 can further include a display 110 and a processing system 115.

In certain implementations, the tracking device 105 can include an infrared camera that identifies the location of position trackers, such as femur and tibia trackers as described herein, to determine the position and orientation of the patient's extremity during, for example, a surgical procedure. For example, the position trackers and the tracking device 105 can be used to identify and provide data relevant to the precise location of the bones in the knee joint. In certain embodiments, the tracking device 105 can detect tracking spheres or other similar markings located on the position trackers in order to gather location data regarding a patient's femur, tibia, or other bone.

In an embodiment, a navigation system 100 can also be used in conjunction with a surgical device having a plurality of position trackers (not shown) to enable the accurate placement and orientation of a cutting block and/or an implant device in accordance with the teachings herein. For example, the navigation system 100 can be used during the surgical procedure to guide and direct the surgeon in order to place an implant within a patient's joint.

In an embodiment, the display 110 of the navigation system 100 can be used to provide feedback information regarding various aspects of the surgical procedure, such as the orientation of the surgical device, the proper location of the implant device, or the like. Further, the processing device 115 of the navigation system 100 can be used to determine the position and orientation of the surgical device with respect to a patient in substantially real time. Additional features and description of the navigation system 100 can be found in, for example, U.S. Pat. Nos. 6,757,582 and 8,961,536, both of which are incorporated herein by reference in their entireties.

Figure 2:
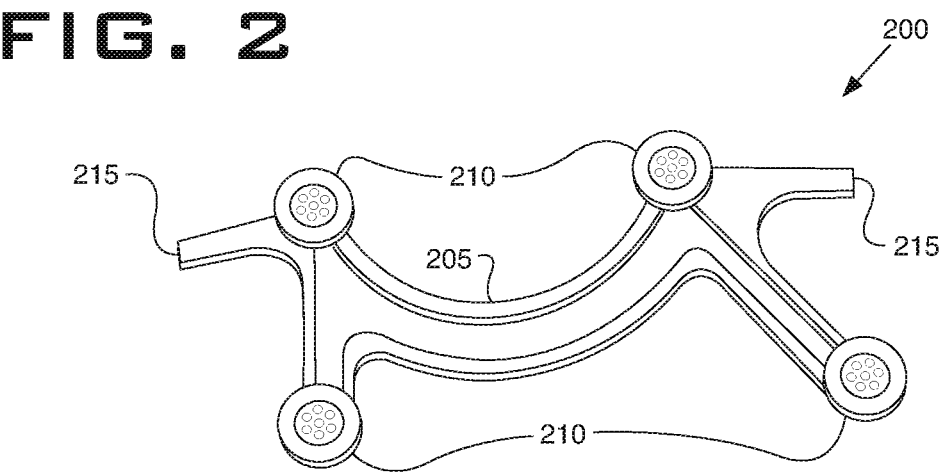
FIG. 2 depicts an illustrative position tracker for use with a navigation system, such as that described in FIG. 1, in accordance with certain embodiments.

FIG. 2 illustrates a sample position tracker 200 similar to those described above in, for example, the discussion of FIG. 1. However, as noted herein, the position tracker 200 can be modified from a standard position tracker. For example, the position tracker 200 can be designed to be mounted to another rigidly fixed component, such as a cut guide. As such, rather than being configured to be pinned directly to a patient's bone (e.g., a patient's tibia), position tracker 200 can be configured to be mounted directly to a tibia cut guide.

As shown in FIG. 2, the position tracker 200 can include a frame 205. The frame 205 can be shaped to accommodate multiple position markers 210. For example, as shown in FIG. 2, a set of four position markers 210 are mounted on the frame 205, positioned at various points about a general periphery of the frame. The position markers 210 can include a reflective portion or another similarly recognizable portion configured to be identified and tracked by a tracking device, such as tracking device 105 as described above in the discussion of FIG. 1.

It should be noted that four position markers 210 are shown in FIG. 2 by way of example only. Depending upon the size and shape of the position tracker 200, alternate numbers of position markers 210 can be used. However, it should be noted that to maintain an accurate measurement of where the position tracker is located and how it is oriented, the position tracker should ideally include multiple position markers such that a navigation system tracking the position tracker has more data points to monitor and track through space. For example, the position markers 210 can be arranged in a pattern known to the navigation system such that the navigation system can accurately determine and track the position and orientation of the position tracker 200 in space.

The frame 205 can further include one or more mounting points 215. As noted above, the position tracker 200 can be configured to mount directly to a cut guide such as a tibia cut guide. In such an implementation, the mounting points 215 can be configured to rigidly fix the position tracker 200 to the cut guide. Depending upon the design of the position tracker 200, the mounting points 215 can be statically designed and configured to be frictionally held in place by, for example, a clamp integrated into or removably attached to the cut guide. In certain implementations, the mounting points 215 can be shaped such that they can only fit into a cut guide in a single position. For example, the mounting points 215 can include grooves, slots, detents, and/or other features that prevent the position tracker 200 from being improperly mounted to a cut guide. In alternate implementations, the position tracker 200 can be configured such that the mounting points 215 include clamps or other similar fixation devices for directly attaching the position tracker to the cut guide.

Figure 3:
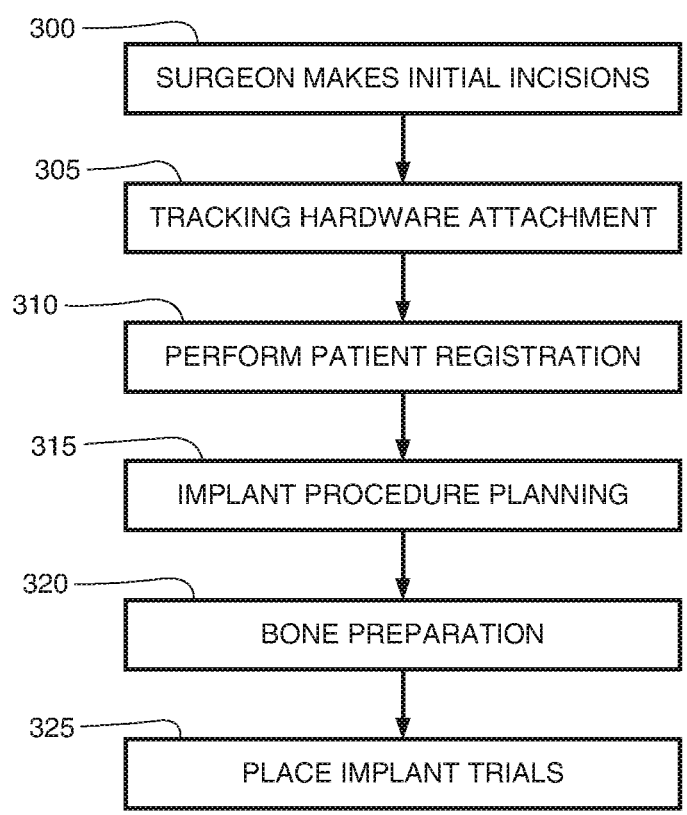
FIG. 3 depicts a flow diagram of an illustrative method of performing a joint replacement surgery in accordance with certain embodiments.

FIG. 3 illustrates a flowchart showing a sample surgical procedure for a total knee replacement. It should be noted that, while the discussion and examples included herein are generally directed to knee replacement procedures, the techniques described herein related to position tracker mounting on a previously mounted component, such as a cut guide, can be incorporated into other computer-assisted surgical procedures where a navigation system such as that described above in regard to FIG. 1 is used.

Referring to FIG. 3, the process as illustrated therein begins after all pre-surgery preparation and planning has already been performed. Following standard approaches and accepted surgical techniques, the surgeon can make 300 the initial surgical incisions on the indicated patient for knee replacement. After the initial incisions, the surgeon can proceed to attach 305 the tracking hardware (e.g., a femur position tracker and a tibia position tracker). Using existing manual tools, which can include the ankle clamp, extramedullary alignment guide and tibia cut guides with resection depth gauge, the surgeon can follow surgical technique guidance to mechanically align the cut guide on the patient's tibia bone. The surgeon utilizes pins to secure the standard tibia cutting guide on the bone surface at this time. The surgeon can further attach femur fixation pins for tracking the femur using the navigation system and use the tibia cutting guide as a fixation base to attach the tibia position tracker.

Figure 4:
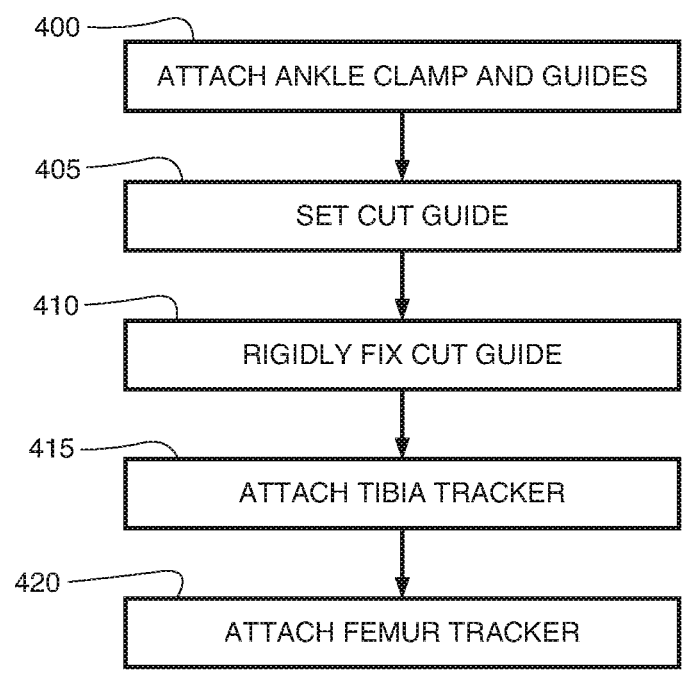
FIG. 4 depicts a flow diagram of an illustrative method of attaching tracking hardware in accordance with certain embodiments.
Figure 5:
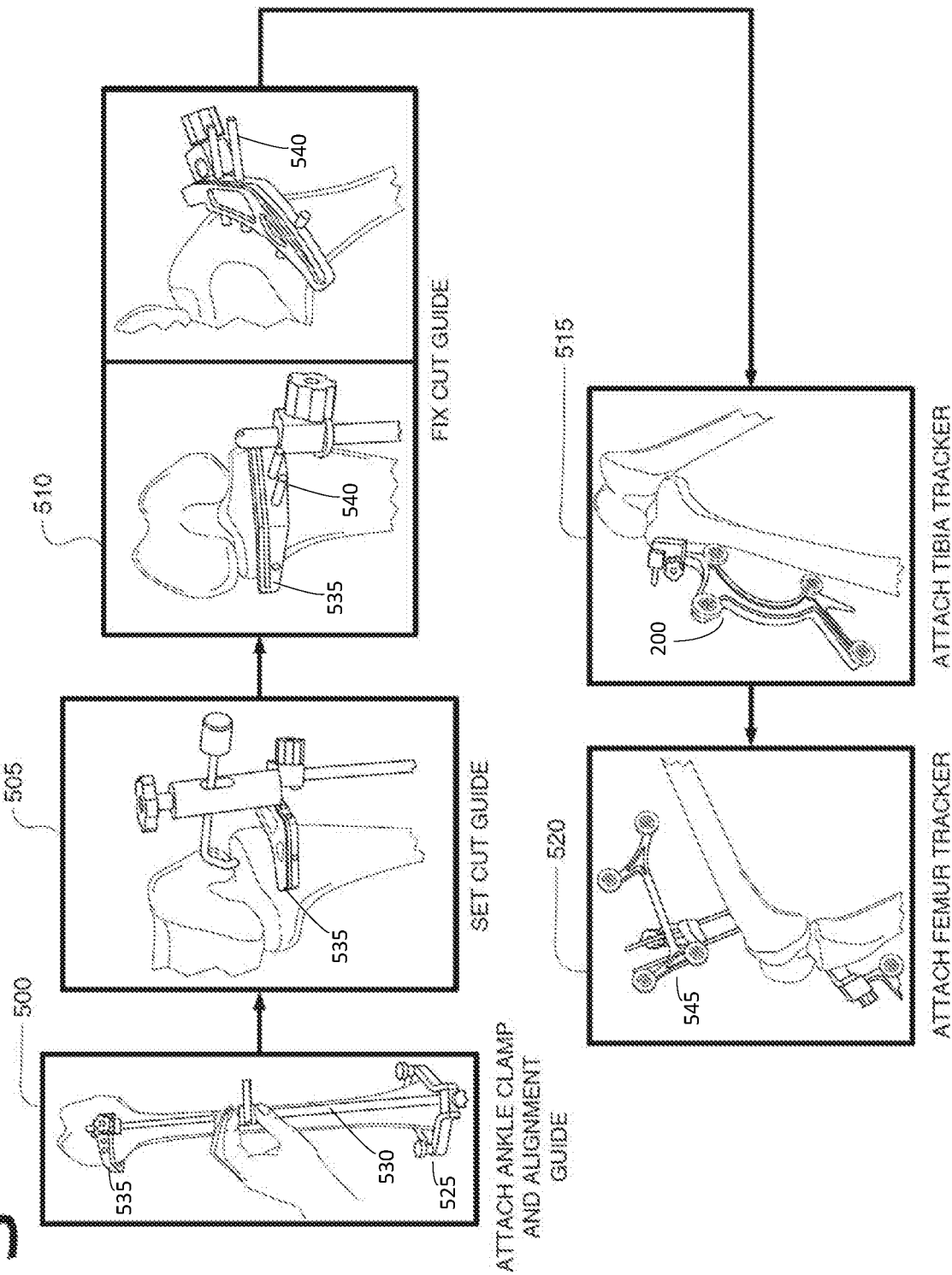
FIG. 5 depicts a similar flow diagram as shown in FIG. 4 further illustrated with annotated photos of attaching the tracking hardware in accordance with an embodiment.

FIGS. 4 and 5 provide additional detail for the position tracker attachment. FIG. 4 illustrates a process for position tracker attachment using a series of process steps, while FIG. 5 illustrates the same process using photos showing the tracker attachment on a skeleton's tibia and femur. The process as shown in FIGS. 4 and 5 can be implemented, for example, during the tracker attachment operation 305 of FIG. 3 as described above.

Referring initially to FIG. 4, the surgeon can attach 400 an ankle clamp and extramedullary alignment guide to the patient's lower leg. The surgeon can rotate and properly position the ankle clamp and guide such that a desired angle and position is achieved. Once the proper angle and position is achieved, the surgeon can set 405 the tibia cut guide. Setting 405 the tibia cut guide can include, for example, setting the desired resection depth, varus/valgus angles, and slope for the tibia. Once the cut guide is set 405, the cut guide can be rigidly affixed 410 to the patient's tibia using pins as described above. The ankle clamp and extramedullary alignment guide can then be removed.

Once the cut guide is rigidly affixed 410, the surgeon can attach 415 the tibia position tracker directly to the mounted cut guide. As noted above in the discussion of FIG. 2, the tibia position tracker can be clamped or otherwise removably attached to the cut guide. The surgeon can then attach 420 the femur position tracker using conventional attachment techniques including, for example, directly pinning the femur position tracker to the patient's femur.

Referring to FIG. 5, in photo 500 an ankle clamp 525 and an alignment guide such as extramedullary alignment guide 530 can be affixed to the patient's lower leg. It should be noted that, while photo 500 shows the ankle clamp 525 attaching directly to the patient's bone, the ankle clamp can be positioned externally on the patient's ankle without any incisions. The surgeon can use their best judgment and experience to properly position the ankle guide 525 at a desired angle and location. For example, the ankle guide 525 can be configured to rotate about the patient's ankle to provide for a proper centered position. The extramedullary alignment guide 530 can then be affixed to the ankle clamp 525 and positioned such that the alignment guide is essentially parallel to the patient's tibia.

As shown in photos 500 and 505, the surgeon can attach the tibia cut guide 535 to the extramedullary alignment guide 530 and set the tibia cut guide to the proper position. As noted above, setting the tibia cut guide 535 to the proper position can include setting the desired resection depth, varus/valgus angles, and slope. As shown in photo 510, one or more cortical pins 540 are inserted into the tibia cut guide 535 to rigidly fix the cut guide to the patient's tibia. As shown in the right of photo 510, the extramedullary alignment guide 525 and ankle clamp 520 have been removed, leaving only the tibia cut guide 535 fixed to the tibia. In photo 515, a tibia position tracker (e.g., tracker 200 as described above) can be attached to the tibia cut guide 535. As shown in photo 515, the position tracker 200 is clamped into the same receptacle that the extramedullary alignment guide 525 was previously attached. In alternate implementations, the tibia cut guide 535 can include a separate attachment point for the position tracker 200.

As shown in photo 520 of FIG. 5, a femur position tracker 545 can be attached to the patient's femur using traditional attachment techniques including, for example, directly pinning the femur position tracker to the patient's femur.

Referring again to FIG. 3, the process can continue with the surgeon beginning the intraoperative procedure with the computer assisted surgical system. The surgeon can perform registration 310 of the patient using the mounted tracking hardware and the navigation system components of the computer assisted surgical system. During registration, attention to detail is critical to achieve high-accuracy registration of the bone model. The surgeon can also register 310 the soft tissue constraints of the knee using, for example, a joint laxity input stage in the intraoperative workflow.

The surgeon, along with the surgical system, can then plan 315 the size and position of the implant components while factoring in the impact on soft-tissue space. This calculation can be at least partially based on the joint laxity definition provided during registration. Because the tibia tracker is rigidly attached to the cut guide for the tibia, the "default" cut plane location based on the guide position can be included in the planning information. In certain implementations, this plane can be determined by placing the tracked plane in the cutting slot of the tibia guide, or it can be derived from a known unique geometric relation between the tibia position tracker and the cutting guide. By knowing the location of the tibia resection plane during this planning stage, the surgeon and/or surgical system can proceed with adjusting the remaining parameters to optimize the knee alignment and balance. Alternately, the surgeon and/or surgical system can manipulate the parameters for the plane to fine tune the implant position for additional slope or depth of resection as needed to virtually balance the joint for desired cut results.

The surgeon can then begin bone preparation 320. The preparation 320 can include bone removal/resection utilizing, for example, computer-assisted techniques for preparing the femur. The surgeon can, for example, insert locking posts on the femur bone using a handheld robotic controlled bur. One or more femur cut guides can then be mounted on the locking posts, and the surgeon can utilize the computer assisted surgical system guides to make saw cuts that replicate the planned position of the femur implant. The surgeon can also cut the tibia using the previously-mounted tibia cut guide. In certain implementations, the surgeon can confirm with the computer assisted surgical system that the tibia cut guide is properly positioned (e.g., at the proper plane and angle). If the position is confirmed, the surgeon can then make the tibia cut. If, for some reason, additional cutting is required, the surgeon can use the handheld robotic controlled bur to fine tune the tibia cut of the tibia implant placement.

Following bone preparation and removal, the surgeon can place 325 the implant trials on the prepared bone, and re-tension the ligaments of the joint to assess achieved joint laxity. At this point, the surgeon can also go back to planning whether to re-adjust the cuts, based on achieved alignment and balance. The surgeon can then execute any additional cuts using, for example, robotic-assisted burring.

It should be noted that the process shown in FIG. 3 and the related process shown in FIGS. 4 and 5 are provided by way of example only. In certain implementations, various process steps can be modified or performed in an alternate order. For example, the surgeon may opt to cut the tibia once the tibia cut guide is fixed to the bone, and prior to attachment of the tibia position tracker. In such an example, the surgeon can also opt to place the implant on the tibia prior to registration. The registration process can then be performed as described above with respect to the femur and remaining soft tissue.

Similarly, during planning, the surgeon can change the position of the femur to balance joint laxity as well as fit anatomy for optimized outcomes (that can already include the tibia implant in the joint laxity). Additionally, in certain implementations, if beneficial for optimal joint balancing and alignment, the surgeon can further adjust the tibia depth, slope, and varus/valgus of cut during the planning stage for robotic-assisted preparation of the final surface during the bone preparation.

Figure 6:
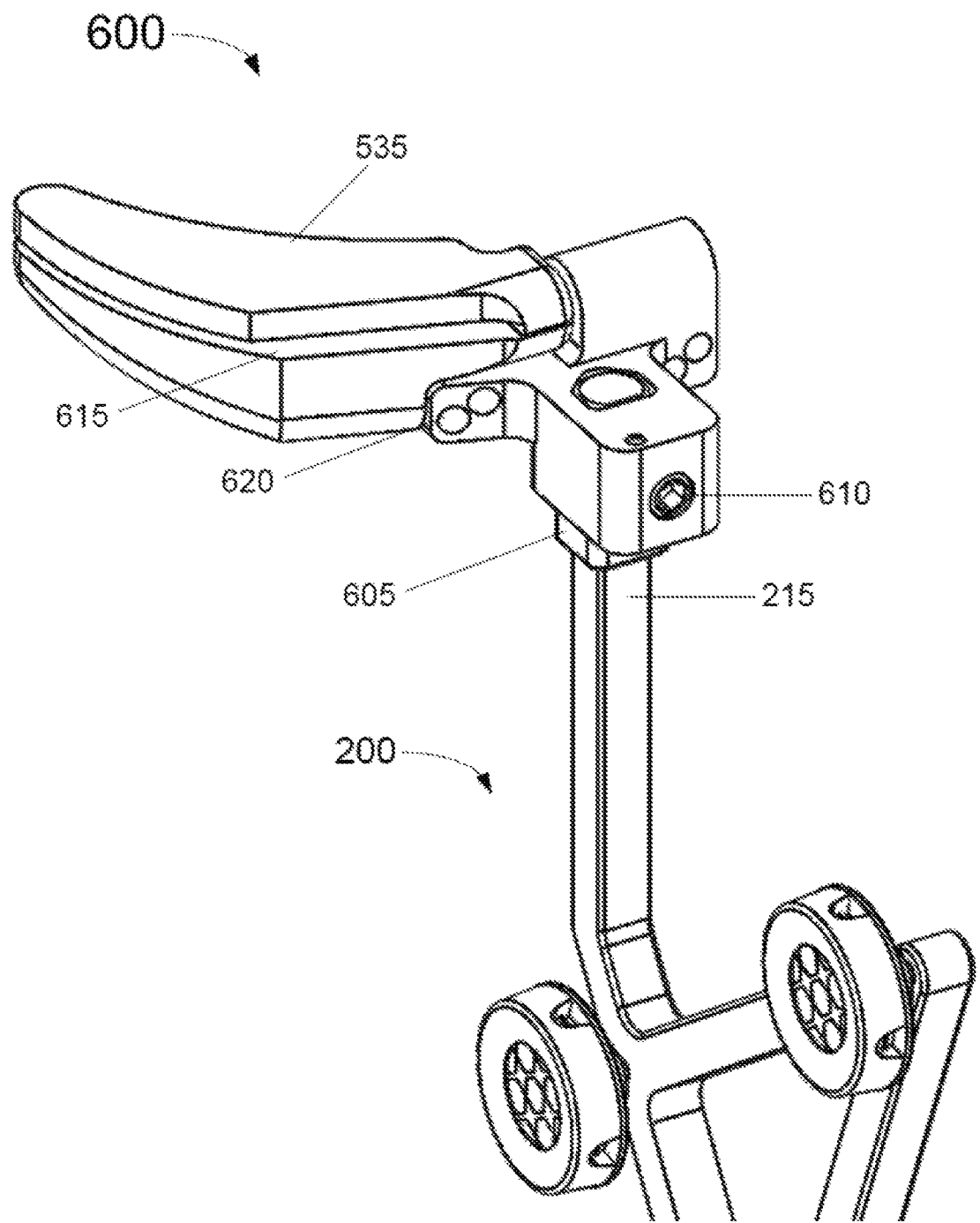
FIG. 6 depicts an illustrative cut guide assembly for use with the position tracker as shown in FIG. 2 in accordance with certain embodiments.

FIG. 6 illustrates a sample cut guide assembly 600. For example, as shown in FIG. 6, the cut guide assembly 600 can include the tibia cut guide 535 and position tracker 200 as described above. In certain implementations, the tibia cut guide 535 can include a receptacle 605 for receiving one or more attachment features and/or mounting points. For example, the receptacle 605 can be configured to receive at least a portion of an alignment guide such as extramedullary alignment guide 530 as described above. In certain implementations, as shown in FIG. 6, the receptacle can be configured to receive the mounting point 215 of the position tracker 200.

In certain implementations, the tibia cut guide 535 can include a locking mechanism 610 configured to lock the cut guide to an object positioned within the receptacle 605. For example, as shown in FIG. 6, the locking mechanism can be configured to lock the mounting point 215 within the receptacle 605, thereby locking the position tracker 200 and the tibia cut guide 535, thereby resulting in cut guide assembly 600. In certain implementations, one or both of the receptacle 605 and the mounting point 215 can include locational features that prevent the mounting point from being improperly inserted into the receptacle. Similarly, one or both of the receptacle 605 and the mounting point 215 can include a stopping feature configured to provide a physical stop when inserting the mounting point into the receptacle, thereby providing for a repeatable insertion process where the same amount of the mounting point is inserted into the receptacle each time the cut guide assembly 600 is assembled.

As further shown in FIG. 6, the tibia cut guide 535 can further include a guide slot 615 configured to guide a cutting device such as a reciprocating saw for creating an initial resection in the patient's tibia. The tibia cut guide 535 can also include, as shown in FIG. 6, a set of pin receptacles 620 configured to receive, for example, bone pins such as cortical pins 540 as described above.

It should be noted that the cut guide assembly 600 as shown in FIG. 6 is provided by way of example only to provide additional detail. Depending upon the application and intended use, the specific components of the cut guide assembly 600 may be altered to provide additional or alternative functionality. For example, the locations of pin receptacles 620 are shown by way of example only. Similarly, locking mechanism 610 is shown as a threaded fastener by way of example only. In certain implementations, the locking mechanism can be implemented in various manners such as a clamping device, a screw, a bolt, a twist-lock fastener, a bayonet fastener, and other similar locking mechanisms.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for mounting a cut guide on a patient during a surgical procedure, the system comprising:
    an ankle clamp configured to clamp to an ankle of a patient;
    an alignment guide configured to be removably attached to the ankle clamp;
    a cut guide comprising:
        a receiving feature configured to removably attach to at least a portion of the alignment guide,
        a locking mechanism configured to lock the receiving feature to the at least a portion of the alignment guide, and
        a plurality of pin receptacles, each of the plurality of pin receptacles configured to receive a bone pin configured to affix the cut guide to a bone of the patient; and
    a position tracker configured to be affixed to the cut guide when the cut guide is affixed to the bone, wherein the position tracker comprises a mounting feature configured to be inserted into the receiving feature of the cut guide upon removal of the at least a portion of the alignment guide, wherein the locking mechanism is further configured to lock the receiving feature to the mounting feature.

2. The system of claim 1, wherein the ankle clamp is configured to adjustably rotate about the patient's ankle to adjust an angle of the alignment guide.

3. The system of claim 1, wherein the alignment guide comprises an extramedullary alignment guide configured to be positioned adjacent to a tibia of the patient.

4. The system of claim 1, wherein the position tracker comprises a plurality of position markers.

5. The system of claim 4, wherein the plurality of position markers comprise reflective markers.

6. The system of claim 4, wherein the position tracker comprises a frame, and wherein the plurality of position markers are mounted on the frame.

7. The system of claim 6, wherein the plurality of position markers are mounted in a known pattern for tracking by a surgical navigation system.

8. The system of claim 1, wherein the cut guide comprises a tibia cut guide.

9. The system of claim 8, wherein the tibia cut guide comprises a guide slot configured to guide a cutting tool to resect a patient's tibia.

10. The system of claim 1, wherein the ankle clamp and the alignment guide are configured to be removed after affixing the cut guide.

11. The system of claim 1, wherein the mounting feature is configured to be inserted into the receiving feature in a single position to prevent improper insertion.

12. The system of claim 1, wherein the mounting feature comprises one or more of a groove, a slot, and a detent.

13. The system of claim 1, wherein the position tracker further comprises a stopping feature to limit a depth of insertion of the mounting feature.

14. The system of claim 1, wherein the receiving feature of the cut guide is configured to receive the mounting feature in a single position to prevent improper insertion.

15. The system of claim 1, wherein the cut guide further comprises a stopping feature to limit a depth of insertion of the mounting feature.

16. The system of claim 1, wherein the cut guide is configured to adjust one or more of resection depth, varus angle, valgus angle, and slope of the bone prior to affixation.

17. The system of claim 1, wherein the locking mechanism comprises one of a clamp, a screw, a bolt, a twist-lock fastener, and a bayonet fastener.

18. The system of claim 1, further comprising a femur position tracker configured to be affixed to a femur of the patient.

19. A system for mounting a cut guide on a patient during a surgical procedure, the system comprising:
- an ankle clamp configured to clamp to an ankle of a patient;
- an alignment guide configured to be removably attached to the ankle clamp;
- a cut guide comprising:
  - a receiving feature configured to removably attach to at least a portion of the alignment guide,
  - a locking mechanism configured to lock the receiving feature to the at least a portion of the alignment guide,
  - a stopping feature, and
  - a plurality of pin receptacles, each of the plurality of pin receptacles configured to receive a bone pin configured to affix the cut guide to a bone of the patient; and
- a position tracker configured to be affixed to the cut guide when the cut guide is affixed to the bone, wherein the position tracker comprises a mounting feature configured to be inserted into the receiving feature of the cut guide upon removal of the at least a portion of the alignment guide, wherein the stopping feature is configured to limit a depth of insertion of the mounting feature.

* * * * *